US008099157B2

(12) United States Patent
Ostrovsky

(10) Patent No.: US 8,099,157 B2
(45) Date of Patent: *Jan. 17, 2012

(54) MEDICAL SCANNING SYSTEM AND RELATED METHOD OF SCANNING

(75) Inventor: Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/855,074

(22) Filed: Aug. 12, 2010

(65) Prior Publication Data

US 2010/0305434 A1 Dec. 2, 2010

Related U.S. Application Data

(63) Continuation of application No. 11/032,228, filed on Jan. 11, 2005, now Pat. No. 7,797,035, which is a continuation of application No. 10/178,413, filed on Jun. 25, 2002, now Pat. No. 6,873,416, which is a continuation of application No. 09/494,709, filed on Jan. 31, 2000, now Pat. No. 6,445,944.

(60) Provisional application No. 60/118,153, filed on Feb. 1, 1999.

(51) Int. Cl.
*A61B 1/07* (2006.01)
*G02B 26/00* (2006.01)

(52) U.S. Cl. ............... 600/476; 600/170; 359/212.2

(58) Field of Classification Search .............. 600/476, 600/101, 129, 137, 170; 359/212.1, 212.2, 359/226.1

See application file for complete search history.

(56) References Cited

U.S. PATENT DOCUMENTS

| | | |
|---|---|---|
| 3,729,248 A | 4/1973 | Beduchaud |
| 4,241,738 A | 12/1980 | Lubbers et al. |
| 4,837,432 A | 6/1989 | Katayama |
| 5,483,343 A | 1/1996 | Iwamoto et al. |
| 5,491,524 A | 2/1996 | Hellmuth et al. |
| 5,537,162 A | 7/1996 | Hellmuth et al. |
| 5,784,186 A | 7/1998 | Wang et al. |
| 5,785,704 A | 7/1998 | Bille et al. |
| 5,891,025 A | 4/1999 | Buschmann et al. |
| 5,904,651 A | 5/1999 | Swanson et al. |
| 5,905,651 A | 5/1999 | Coulibaly et al. |
| 5,943,133 A | 8/1999 | Zeylikovich et al. |
| 6,201,989 B1 | 3/2001 | Whitehead et al. |
| 6,445,944 B1 | 9/2002 | Ostrovsky |
| 6,485,413 B1 | 11/2002 | Boppart et al. |
| 6,501,551 B1 | 12/2002 | Tearney et al. |
| 6,564,087 B1 | 5/2003 | Pitris et al. |

*Primary Examiner* — Jacqueline Cheng

(74) *Attorney, Agent, or Firm* — Finnegan, Henderson, Farabow, Garrett & Dunner, LLP

(57) ABSTRACT

The present invention is directed to a scanning system that uses uniform rotary motion of an optical reflector to create reciprocal linear scanning. The system converts uniform rotation into uniform longitudinal scanning. The system thereby creates mechanical reciprocal linear scanning free of reciprocally moving mechanical parts common in conventional scanning systems. In a preferred embodiment of the invention, the scanning system is incorporated within an imaging catheter for medical scanning. The optical reflector is rotatable and includes a spiral reflecting portion. The spiral reflecting portion may be a single uniform reflecting surface or may include several reflection surfaces arranged in a spiral configuration.

23 Claims, 5 Drawing Sheets

REFLECTOR IN 0° POSITION

REFLECTOR TURNED 45°

REFLECTOR TURNED 90°

REFLECTOR TURNED 135°

REFLECTOR TURNED 179°

MEDICAL SCANNING SYSTEM AND RELATED METHOD OF SCANNING

This application is a continuation of application Ser. No. 11/032,228, filed Jan. 11, 2005 now U.S. Pat. No. 7,797,035, which is a continuation of application Ser. No. 10/178,413, filed Jun. 25, 2002, (now U.S. Pat. No. 6,873,416), which is a continuation of application Ser. No. 09/494,709, filed Jan. 31, 2000, (now U.S. Pat. No. 6,445,944), and claims the benefit of U.S. Provisional Application No. 60/118,153, filed Feb. 1, 1999. Each of these applications is incorporated herein by reference in its entirety.

BACKGROUND OF THE INVENTION

1. Field of the Invention

The present invention relates to a medical scanning system and a related method of scanning. More particularly, this invention relates to a medical scanning system and a related method that uses uniform rotary motion of an optical reflector to create reciprocal linear scanning.

2. Background of the Related Art

Various types of medical imaging techniques are currently used for diagnosis and treatment of a patient. These imaging techniques include ultrasound imaging and Optical Coherence Tomography (OCT). Ultrasound uses sound waves to obtain a cross-sectional image. These waves are radiated by a transducer and directed into the tissues of a patient. Waves reflected from tissues at different depths excite the same transducer, which now acts as a receiver. The transducer converts the reflected waves into electrical signals, which are electronically processed and ultimately displayed. The typical tissue depth applicable to ultrasound imaging varies, depending on the application, from millimeters to centimeters.

OCT uses electrical light to obtain a cross-sectional image of tissue. Since light waves are faster than sound waves, OCT takes a different approach to imaging. The depth of tissue scan in OCT is based on low coherence interferometry. Low coherence interferometry measures the field of an optical beam rather than its intensity. It preferably uses an interferometer with reference arm scanning and a low coherence light source. In use, a low coherence light source of the interferometer is directed onto a beam splitter to produce two beams, a sampling measurement beam and a reference beam. The sampling beam hits and penetrates the tissue or material to be imaged, and then reflects (backscatters) from the tissue, carrying information about the reflecting points from the surface and the depth of the tissue. The reference beam hits a reference reflector, for example a mirror or a diffraction grating, and reflects from the reference reflector. The reference beam travels a given path length, such that the reference reflector either moves or is designed such that the reflection occurs at different distances from the beam splitting point and returns at a different point in time or in space, which actually represents the depth scanning. The amount of such movement represents the desirable depth of penetration of the tissue or object being imaged by the sampling beam. Typical such depths in OCT are 2 to 3 millimeters.

The output of the interferometer is the superposition of the electromagnetic fields from the reflected reference beam and the sampling beam reflected from the tissue or material being imaged. When the reflected beams meet, interference is observed only where the path lengths of the reference arm and sampling arm are matched to within the coherence length of the light. A photodetector detects this interference and converts it into electrical signals. The signals are electronically processed and ultimately displayed, for example, on a computer screen or other monitor.

Each cross-sectional image involves two scans: depth (axial) and width (lateral). Typically, the rate of depth scan is faster than the rate of lateral scan, as 200 to 300 or more depth scans may occur for one lateral scan during live imaging. A typical rate of lateral scanning during live imaging is approximately 26-30 scans per second.

A typical OCT probe for linear cross sectional imaging uses a mechanical scanning arrangement in which at least one mechanical part reciprocates to create a scanning motion. The reciprocal motion, however, creates drawbacks associated with the inertia of moving parts. These drawbacks affect the accuracy of the scan. For example, reciprocal motion involves nonuniform speed of scan, i.e. the scanning speed decreases to zero at the end of each reciprocating cycle. In addition, vibration of the reciprocating mechanical parts results in an unstable scanning system and an elevated level of electronic noise. These problems increase as the scanning speed increases during live imaging.

SUMMARY OF THE INVENTION

In light of the drawbacks of the scanning systems described, there is a need for a scanning system which allows for better accuracy of scans at all speeds during live imaging. Accordingly, the present invention is directed to an improved device that obviates the limitations and disadvantages of conventional scanning systems.

To achieve these and other advantages and in accordance with the present invention, as embodied and broadly described herein, a scanning system is provided. The scanning system includes a light source for emitting a beam of light to be split into a reference beam and a sampling beam, a reference reflector for receiving and reflecting the reference beam, and a rotatable sampling reflector for receiving and reflecting the sampling beam.

In another embodiment of the invention, an imaging catheter is provided. The imaging catheter includes a catheter having a proximal end and a distal end, the catheter connected to a housing at the distal end of the catheter, the catheter including a light path for receiving and passing light from a light source, and a rotatable sampling reflector suspended within the housing so that the sampling reflector receives light from the light path.

According to one aspect of the invention, a method of scanning an object using optical coherence tomography. The method includes directing a light beam from a light source onto a rotating sampling reflector, reflecting the light beam off a surface of the rotating sampling reflector into an object to be scanned, and receiving the light beam reflected from the object.

Additional features and advantages of the present invention will be set forth in the description which follows, and in part will be apparent from the description, or may be learned by practice of the invention. The objectives and advantages of the invention will be realized and attained by means of the elements and combinations particularly pointed out in the appended claims.

BRIEF DESCRIPTION OF THE DRAWINGS

The accompanying drawings, which are incorporated in and constitute a part of this specification, illustrate various embodiments of the invention and together with the description, serve to explain the principles of the invention. In the drawings.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

The present invention is directed to a scanning system and related method of scanning that uses uniform rotary motion of an optical reflector to create reciprocal linear scanning. The system converts uniform rotation into uniform longitudinal scanning. The system thereby creates mechanical reciprocal linear scanning free of reciprocally moving mechanical parts common in conventional scanning systems.

Figure 3:
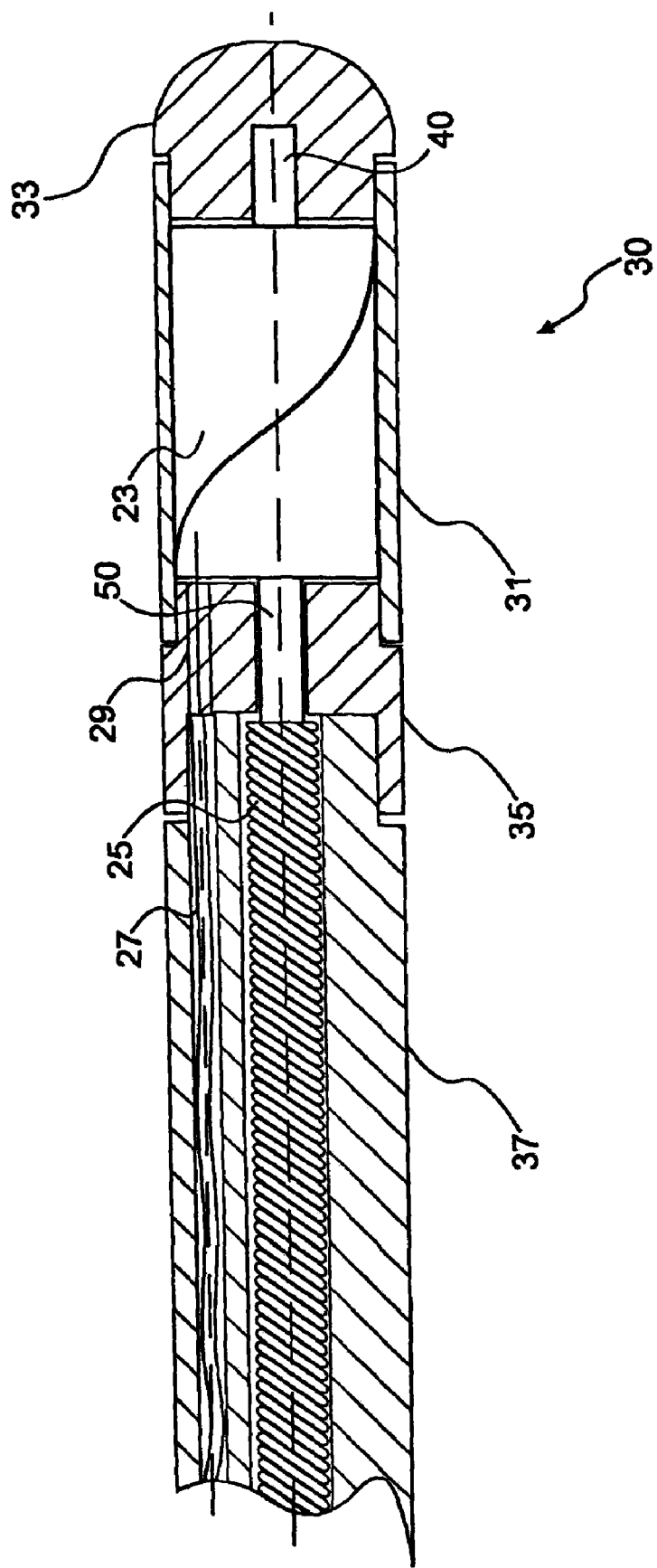
FIG. 3 is a cross-sectional side view of a distal end of an image catheter incorporating a spiral sampling reflector and scanning system according to the present invention.

The scanning system according to the present invention has particular application in medical devices and more particularly in medical imaging catheters placed within a lumen of an endoscope or other like device that aids in the guidance of the catheter. The scanning system therefore is described in connection with such a medical imaging catheter, as shown in FIG. 3. However, such a catheter can be used with or without an endoscope and in other medical applications, including vascular or nonvascular systems of a patient. In addition, a scanning system in accordance with the present invention may be used in connection with non-medical imaging devices.

The scanning system according to an embodiment of the present invention includes a thread-like or spiral-like sampling reflector and a light source. The light source sends a collimated light beam onto the sampling reflector. The sampling reflector rotates uniformly so that the incident light beam reflects uniformly in linear motion.

FIGS. 1A to 1E show an embodiment of a spiral sampling reflector 1 for use in a canning system according to the present invention. Reflector 1 has two mirror or reflector surfaces 7 and 9, the reflector surfaces preferably comprising identical surface material. Reflector 1 has a length 11, a diameter 12, an angle of spiral 13, and an angle of reflection 14. Both angles of spiral and reflection 13 and 14 are measured with respect to a line parallel to a longitudinal axis 3 of the spiral sampling reflector 1. Length 11 is defined by the field of interest and desirable lateral resolution. The diameter of the catheter restricts the size of diameter 12 of the reflector 1.

For use in a typical OCT imaging catheter, such as the catheter shown in FIG. 3, reflector 1 has a length 11 of approximately 2 to 3 millimeters. Diameter 12 of reflector 1 may, for example, be approximately 1 millimeter. For a reflector 1 of such size, and according to laws of geometry and reflection, angle of spiral 13 would be approximately 38 to 27 degrees (respectively for a length of 2 to 3 mm) and angle of reflection 14 would be approximately 76 to 54 degrees (respectively for a length of 2 to 3 mm). In the embodiment of the invention shown in FIGS. 1A to 1E, the angle of reflection 14 directly depends on spiral angle 13. Materials for reflector 1 may include, for example, aluminum, or any other suitable reflecting material known in the scanning art.

Figure 1A:
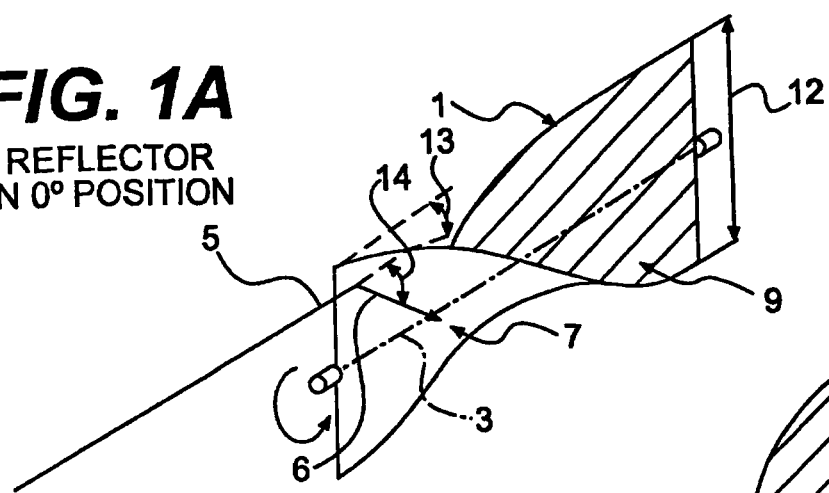
FIGS. 1A to 1E are perspective views of an embodiment of a spiral sampling reflector for use in a scanning system according to the present invention.
Figure 1B:
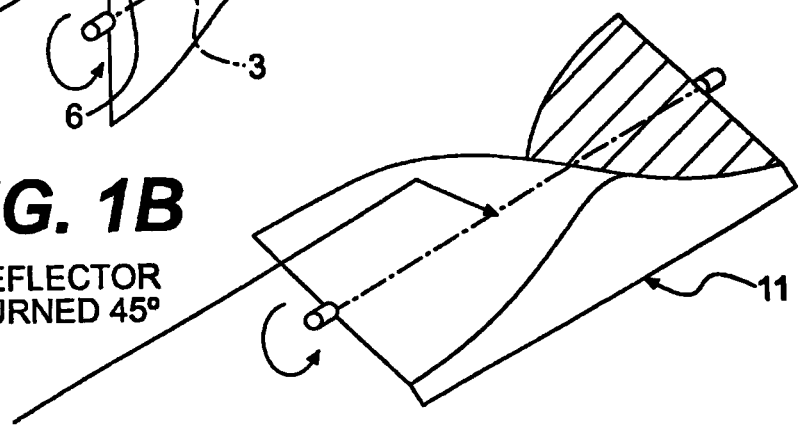
Figure 1C:
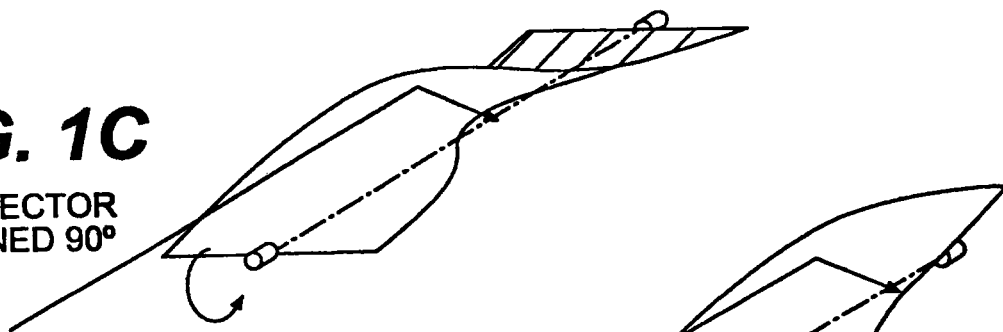
Figure 1D:
Figure 1E:
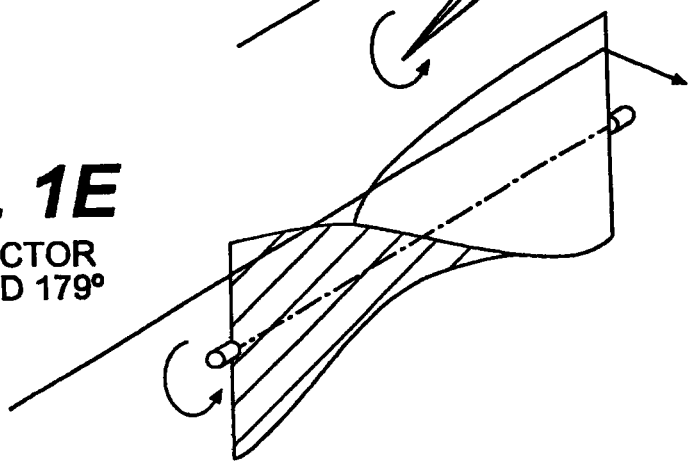

Spiral sampling reflector 1 is suspended along longitudinal axis 3 by any suitable mechanical parts. In use, a beam of incident light 5, parallel to axis 3 of sampling reflector 1, shines onto reflector 1 and reflects off of reflector surface 7 as reflected beam 6. FIGS. 1A to 1E show spiral sampling reflector 1 progressing through half of a full rotation. FIG. 1A shows reflector 1 in a position just greater than 0 degrees. In this position, incident light beam 5 hits an extremely left side of reflector surface 7. In a 0 degree position, light beam 5 actually hits an end of reflector 1. FIGS. 1B to 1E show the counterclockwise progression of spiral reflector 1 at approximately 45 degree intervals. Clockwise rotation will produce the same scanning, except in opposite directions. As shown in FIG. 1E, incident light beam 5 hits an extremely right side of reflector surface 7 when the reflector is just completing a half rotation. A half rotation completes one full sweep of reflected light beam 6. The next 45 degree rotation of reflector 1 places reflector 1 in the position shown in FIG. 1A, but with reflector surface 9 receiving light beam 5. This instantly returns reflected beam 6 into the initial scanning position for the next scanning sweep to begin. Thus, a full rotation of reflector 1 corresponds to two longitudinal sweeps of reflected light beam 6.

Figure 2A:
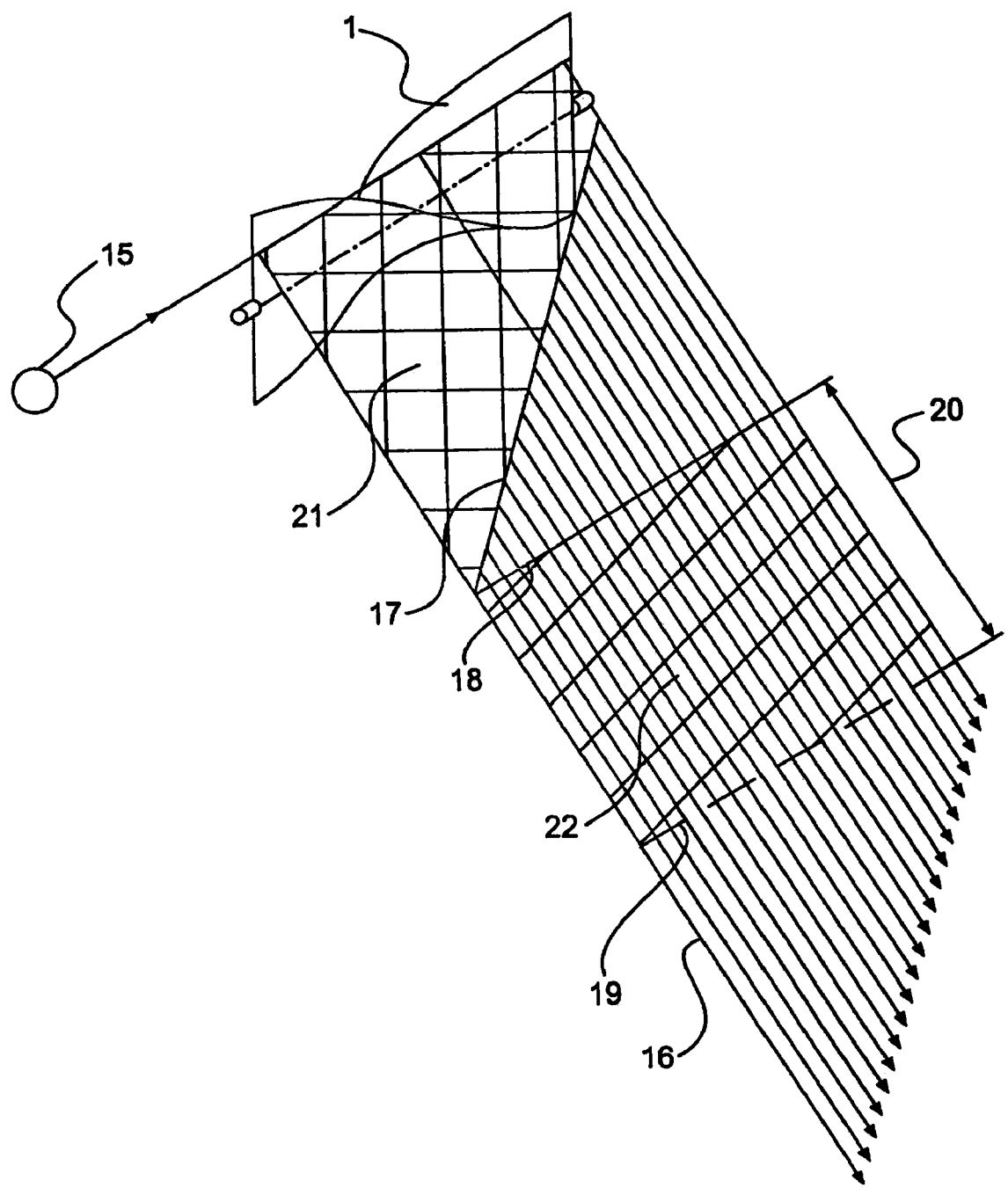
FIG. 2A is a perspective view of the spiral sampling reflector of FIGS. 1A-1E with a light source, graphically showing a representative scanning area.

In a scanning system according to the present invention, the optical path from the light source to the reflector continuously changes. More particularly, as shown in FIG. 2A, the distance from a light source 15 to a reflecting point on spiral reflector 1 changes as reflector 1 rotates. This causes the starting points of depth scanning vectors 16 to change positions with respect to reflector 1. Line 17 represents positions of those starting points. This creates a dead zone 21, which has a triangular shape. An object or a part of an object within zone 21 will not be scanned and therefore will not be seen on the display. This may be overcome by offsetting the field of view away from the reflector 1 by the distance equal to the largest side of dead zone 21 (to the left in FIG. 2A). This may be accomplished by, for example, placing a spacer between reflector 1 and the object to be scanned. Such a spacer would force the actual scanning to start at line 18. A depth of view 20, between line 18 and an end of depth scanning line 19, is limited by the system design. Typically for OCT, depth of view 20 is between approximately 2 and 3 millimeters.

A second approach to overcoming the change in optical path of the sampling arm is to introduce the same change in optical path in the reference arm.

Figure 2B:
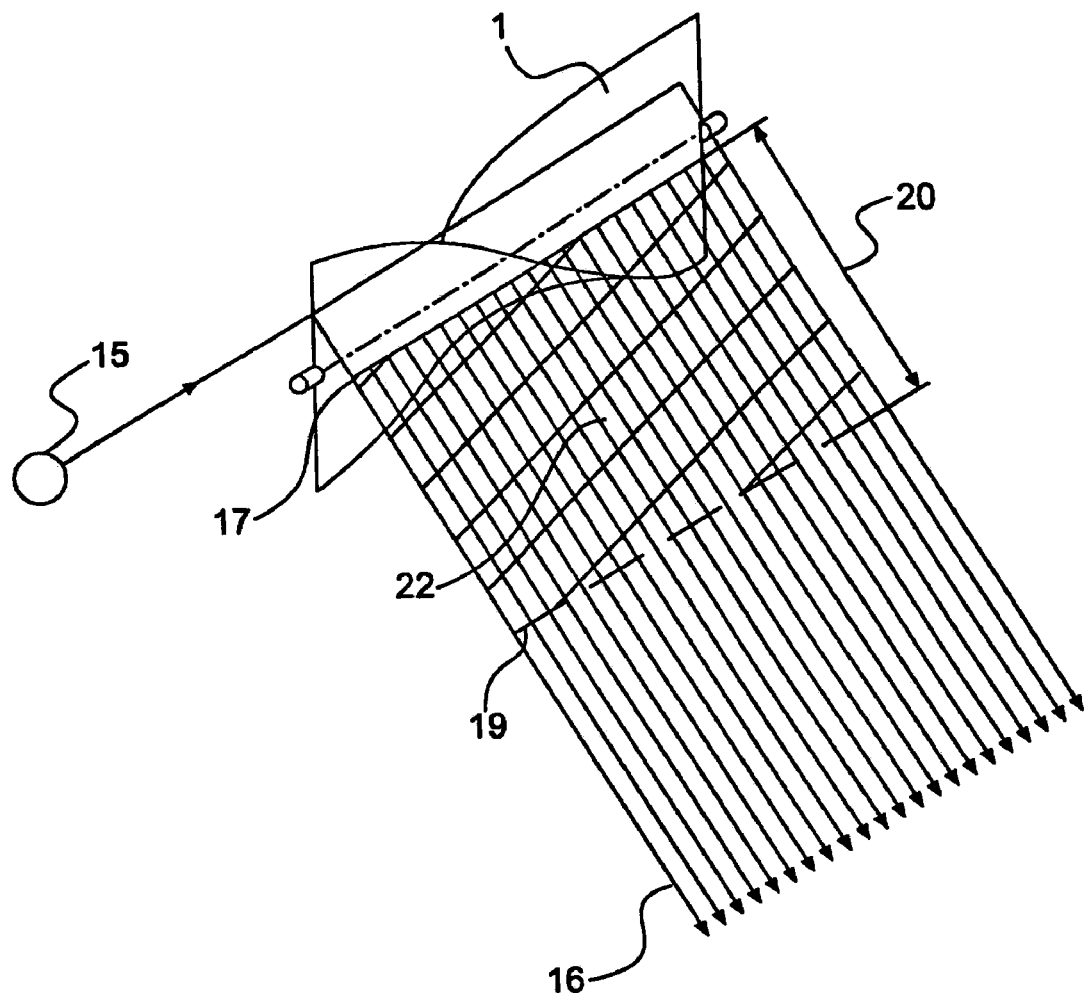
FIG. 2B is a perspective view of the spiral sampling reflector of FIGS. 1A-1E with a light source, also graphically showing a representative scanning area.

More particularly, in OCT, this is achieved by adjusting the optical path in the reference arm of the interferometer by, for example, making a reference reflector similar to the scanning reflector and spinning the reference reflector in synch with the scanning reflector. In this case, line 17, shown in FIG. 2B representing the positions of starting points of depth scan vectors, is parallel to the reflector axis 3.

In use, the low coherence light source of the interferometer is directed onto a beam splitter to provide two beams, a sampling beam and a reference beam. As spiral sampling reflector 1 rotates, the sampling beam is directed parallel to the longitudinal axis 3 of the spiral sampling reflector 3. The sampling beam hits the spiral reflector 1 and reflects from a reflector surface 7 of the reflector as the reflector rotates, hits and penetrates the tissue, or any object to be imaged, and then reflects from the tissue or object to be imaged, back to sampling reflector 1, carrying information about the reflecting points from the surface and the depth of the tissue or object being imaged. The spiral sampling reflector 1 need rotate only about 180 degrees to complete a single lateral sweep of the sample. If the spiral sampling reflector rotates beyond 180 degrees, a second lateral sweep of the sample begins, this time with the light beam being reflected off of reflector surface 9 of reflector 1. As the spiral reflector rotates, the reflection occurs at different points along the longitudinal axis of the reflector, completing the reciprocal lateral scan of the sample.

At the same time, the other portion of the split beam, the reference beam, is directed to the reference reflector, which may or may not be a spiral reflector 1. This reflector typically moves back and forth very rapidly to scan the depth of the sample. Typically, 200-300 or more depth scans occur during one lateral sweep. If a spiral reflector is used, it has to additionally rotate in synch with spiral sampling reflector 1 to compensate for the optical path change. If a spiral reflector is not used, measures will have to be taken to compensate for the triangular dead zone 21, discussed above with reference to FIGS. 2A and 2B.

When the reflected beams meet, interference is observed only where the path lengths of the reference arm and sampling arm are matched to within the coherence length of the light. A photodetector (not shown) detects this interference and converts it into electrical signals. The signals are electronically processed and ultimately displayed, for example, on a computer screen or other monitor.

FIG. 3 shows a distal end of an image catheter 30 incorporating a spiral reflector 23 and scanning system according to the present invention. In this embodiment, the catheter becomes a part of the sampling arm of the interferometer. Spiral reflector 23, preferably made of aluminum, rotates freely about its longitudinal axis within a rigid surrounding housing. The housing includes three main parts: a transparent cover 31, an end tip 33, and an adapter 35. Cover 31 rigidly connects tip 33 to adapter 35 to form the rigid housing. Tip 33 and adapter 35 serve as bearings in which reflector 23 is suspended. Tip 33 preferably includes a rounded end and a central hole partially there through for receiving a pin 40. Pin 40 is mechanically coupled to and rotatable with reflector 23. Adapter 35 includes a central hole for receiving a pin 50. Pin 50 couples a central drive shaft 25 of catheter 30 to reflector 23. Drive shaft 25, preferably made of a metal wire coil, rotates reflector 23. Transparent cover 31, tip 33, and adapter 35 are each preferably made of polycarbonate or any other suitable biocompatible material.

An optical fiber 27 delivers light energy that is then collimated by a GRIN lens 29. The collimated light beam hits reflector 23 as reflector 23 rotates. The light beam is reflected off of reflector 23 and passes through transparent cover 31 to the object being scanned. Adapter 35 includes a second through hole for containing collimator 29. Adapter 35 attaches to a flexible catheter sheath 37, preferably made of a flexible plastic such as nylon. Sheath 37 has an outer diameter of approximately 2.5 mm so that catheter 30 fits within a working lumen of an endoscope. Sheath 37 includes two channels: a central channel of approximately ¾ mm diameter for drive shaft 25, and a side channel of approximately ¼ mm diameter for optical fiber 27.

The proximal end of catheter 30 (not shown) includes various connections. For example, the proximal end connects to any suitable source of mechanical rotation to transmit a torque to drive shaft 25 and ultimately to reflector 23. In addition, the proximal end connects to a source of light to transmit light through optical fiber 27 to reflector 23. The catheter also couples to appropriate processing devices to process and modify, as appropriate, the optical light reflected from the tissue. Such processing devices may generally include, for example, an optical detector, a digitizer, and other electronic circuitry, so that the optical light reflected from the tissue ultimately becomes an image on a monitor.

Figure 4:
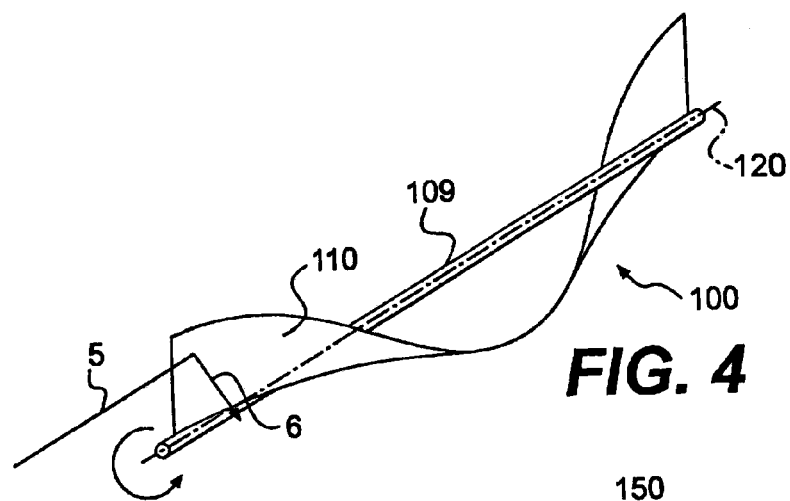
FIG. 4 is a perspective view of another embodiment of a spiral sampling reflector for use in a scanning system according to the present invention.

FIG. 4 shows another embodiment of a spiral reflector 100 for use in a scanning system according to the present invention. Spiral reflector 100 includes only one reflector or mirror surface 110 from which an incident light beam 5 reflects. Reflector 100 may be supported by a rod-like structure 105 that rotates about a longitudinal axis 120 of reflector 100. As can be seen from FIG. 4, the tightness of the spiral of the spiral sampling reflector 100 is not formed in as "tight" a spiral as is spiral sampling reflector 1. Reflector 100 makes a full 360 degrees spiral about its longitudinal axis 120. Therefore, a full 360 degree rotation is required to complete one longitudinal scanning sweep. Reflector 100 must spin twice as fast as reflector 1 (shown in FIGS. 1A-1E) to maintain the same scan rate. The length of the reflector 100 may remain the same as that of reflector 1 because its length is set according to the desired application. The angle of spiral and angle of reflection for reflector 100, which are measured with respect to the longitudinal axis 120, will differ from those of reflector 1 even if the lengths are the same. For example, in a reflector having a scan length of approximately 3 millimeters and a reflector diameter of approximately 1 millimeter, using simple geometry and the law of reflection, the angle of spiral for reflector 100 would be approximately 46 degrees (as opposed to 27 degrees for reflector 1) and the angle of reflection approximately 92 degrees (as opposed to 54 degrees for reflector 1).

Figure 5A:
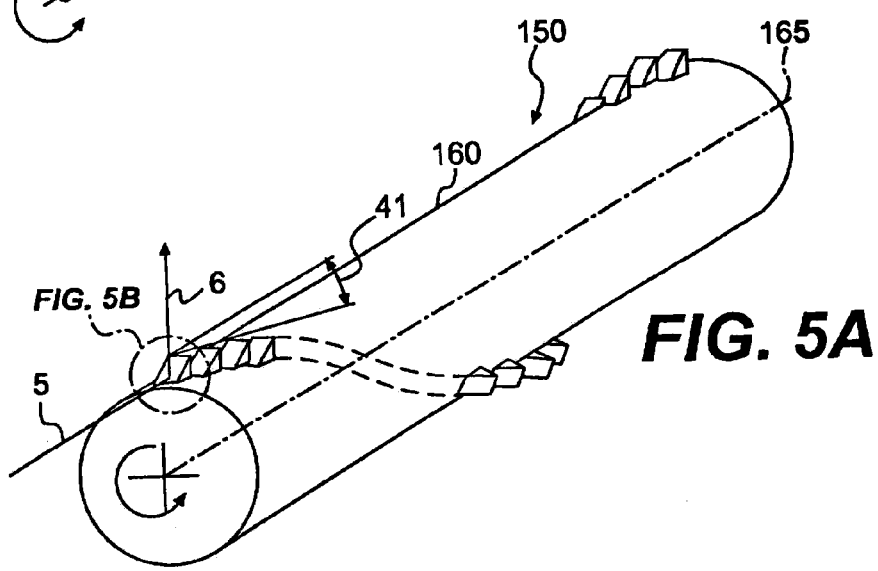
FIG. 5A is a perspective view of a further embodiment of a spiral sampling reflector for use in a scanning system according to the present invention.
Figure 5B:
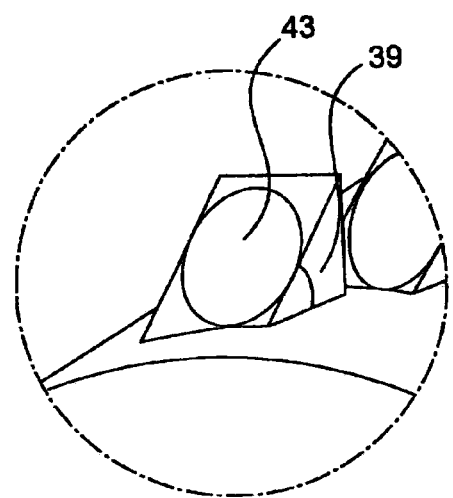
FIG. 5B is an exploded perspective view of a reflecting surface of the spiral sampling reflector shown in FIG. 5A.

FIGS. 5A and 5B show a further embodiment of this invention. In this embodiment, as opposed to the reflectors in FIGS. 1A to 4, the reflecting surface is not a spiraled material and the angle of reflection is not dependent on the angle of spiral. Because the reflecting surface is not a spiral, the surface better provides for a tight (and not spread) beam of reflected light.

As shown in FIGS. 5A and 5B, spiral reflector 150 includes a plurality of reflector surfaces 43 arranged about a cylinder-like structure 160 in a spiral configuration. Each reflector surface 43 may be supported by a triangular shaped support structure, as shown in FIGS. 5A and 5B, or any other suitable support structure. The spiral configuration of surfaces 43 includes an angle of spiral 41. This angle of spiral is defined in the same manner as that of the spiral reflector shown in FIG. 4, since it takes a full 360 degree rotation of cylinder 160 to complete one scanning sweep of reflector 150.

Reflecting surface 43 itself, however, is not a part of a spiral and is independent of the angle of spiral. The angle of reflection is defined by the position of surface 43 with respect to the axis 165 and the surface of cylinder 160 (i.e., a straight line at the surface of cylinder 160 which is parallel to axis 165). This angle can be set according to the requirements for a desired application. FIG. 5B, for example, shows an angle 39, between surface 43 and surface 160. According to the laws of reflection, the angle of reflection is two times greater than angle 39. Thus, it is possible to control the angle of reflection by setting the surface 43 at a desired angle with respect to axis 165.

Since each reflector surface 43 is discreet, reflector surface 43 can be of any shape, for example flat, spherical, or otherwise. The shape depends on the shape of the reflected beam required by the application, for example, collimated or focused.

The method of use for reflectors 100, 150 is essentially the same as discussed above. In use, the low coherence light source of the interferometer is directed onto a beam splitter to provide two beams, a sampling beam and a reference beam. As spiral sampling reflector 100, 150 rotates, the sampling beam is directed parallel to the longitudinal axis 120, 165 of the spiral sampling reflector 100, 150 (through the optical fiber in the case of the imaging catheter). The sampling beam hits the spiral reflector 1 and reflects from a reflector surface 110, 43 of the reflector 100, 150 as the reflector rotates. The sampling beam then reflects off of reflector surface 110, 43, (and in the case of the imaging catheter passes through transparent cover 31), hits and penetrates the tissue, or any object being imaged, and then reflects from the tissue or object being imaged, back to sampling reflector 100, 150, carrying information about the reflecting points from the surface and the depth of the tissue or object being imaged. The reflector 100, 150 must complete a 360 degree rotation to complete one laterall sweep of the sample (unlike the method described above for reflector 1). As the spiral reflector rotates, the reflection occurs at different points along the longitudinal axis of the reflector, completing the reciprocal lateral scan of the sample.

At the same time, the other portion of the split beam, the reference beam, is directed to the reference reflector, which may or may not be a spiral reflector 100, 150. This reflector typically moves back and forth very rapidly to scan the depth of the sample. Typically, 200-300 or more depth scans occur during one lateral sweep. If a spiral reflector is used, it has to additionally rotate in synch with spiral sampling reflector 100, 150 to compensate for the optical path change. If a spiral reflector is not used, measures will have to be taken to compensate for the triangular dead zone 21, discussed above with reference to FIGS. 2A and 2B.

When the reflected beams meet, interference is observed only where the path lengths of the reference arm and sampling arm are matched to within the coherence length of the light. A photodetector (not shown) detects this interference and converts it into electrical signals. The signals are electronically processed and ultimately displayed, for example, on a computer screen or other monitor.

It will be apparent to those skilled in the art that various modifications and variations can be made in the medical scanning device and system of the present invention and in construction of the medical scanning device and system without departing from the scope or spirit of the invention.

Other embodiments of the invention will be apparent to those skilled in the art from consideration of the specification and practice of the invention disclosed herein. It is intended that the specification and examples be considered as exemplary only.

What is claimed is:

1. A medical scanning system comprising:
a light source configured to emit a beam of light;
a rotatable reflector configured to reflect the beam of light into body tissue to be scanned, wherein rotation of the reflector causes a change in optical path length of the beam of light and creates a dead zone, such that an object lying within the dead zone is not scanned; and
a spacer configured to be positioned between the reflector and the tissue so that scanning of the tissue starts a predetermined distance from the reflector, thereby compensating for the dead zone.

2. The medical scanning system of claim 1, wherein the reflector comprises a spiral reflector having a first reflector surface and a second reflector surface, the second reflector surface being opposite the first reflector surface.

3. The medical scanning system of claim 1, wherein the reflector comprises a spiral reflector having only one reflector surface.

4. The medical scanning system of claim 1, wherein the reflector comprises a spiral reflector having a plurality of reflector surfaces arranged in a spiral configuration about a cylindrical body.

5. The medical scanning system of claim 1, further comprising:
a catheter through which the beam of light is reflected into the tissue.

6. The medical scanning system of claim 5, wherein the spacer comprises a cover that is connected to a sheath of the catheter, and the beam of light is reflected through the spacer into the tissue.

7. A medical scanning system comprising:
a light source configured to emit a beam of light;
a beam splitter configured to split the beam of light into a reference beam and a sampling beam;
a rotatable spiral sampling reflector configured to reflect the sampling beam into body tissue to be scanned, wherein rotation of the spiral sampling reflector causes a change in optical path length of the sampling beam; and
a reference reflector configured to reflect the reference beam, the reference reflector being configured to cause a change in optical path length of the reference beam that is the same as the change in optical path length of the sampling beam.

8. The medical scanning system of claim 7, wherein the spiral sampling reflector comprises a first reflector surface and a second reflector surface, the second reflector surface being opposite the first reflector surface.

9. The medical scanning system of claim 7, wherein the spiral sampling reflector comprises only one reflector surface.

10. The medical scanning system of claim 7, wherein the spiral sampling reflector comprises a plurality of reflector surfaces arranged in a spiral configuration about a cylindrical body.

11. The medical scanning system of claim 7, wherein the reference reflector comprises a spiral reflector, and the reference reflector and the spiral sampling reflector are rotated in synchronization with one another.

12. The medical scanning system of claim 7, further comprising:
a catheter through which the beam of light is reflected into the tissue.

13. A method of scanning body tissue in a medical procedure, comprising:
directing a light beam onto a reflector;
rotating the reflector to reflect the light beam into the tissue, wherein rotation of the reflector causes a change in optical path length of the light beam and creates a dead zone, such that an object lying within the dead zone is not scanned; and
placing a spacer between the reflector and the tissue so that scanning of the tissue starts a predetermined distance from the reflector, thereby compensating for the dead zone.

14. The method of claim 13, wherein directing the light beam comprises directing the light beam about parallel to a rotational axis of the reflector.

15. The method of claim 13, wherein the reflector comprises a spiral reflector having a single reflector surface.

16. The method of claim 13, wherein the reflector comprises a spiral reflector having a plurality of reflector surfaces.

17. The method of claim 13, wherein the spacer comprises a cover that is connected to a sheath of a catheter, and wherein rotating the reflector comprises rotating the reflector to reflect the light beam through the spacer into the tissue.

18. A method of scanning body tissue in a medical procedure, comprising:
- splitting a light beam into a reference beam and a sampling beam;
- directing the sampling beam onto a spiral sampling reflector;
- directing the reference beam onto a reference reflector;
- rotating the spiral sampling reflector to reflect the sampling beam into the tissue, wherein rotation of the spiral sampling reflector causes a change in optical path length of the sampling beam; and
- compensating for the change in optical path length of the sampling beam by causing the same change in optical path length of the reference beam.

19. The method of claim 18, wherein directing the sampling beam comprises directing the sampling beam about parallel to a rotational axis of the spiral sampling reflector.

20. The method of claim 18, wherein the spiral sampling reflector comprises only one reflector surface.

21. The method of claim 18, wherein the spiral sampling reflector comprises a plurality of reflector surfaces.

22. The method of claim 18, wherein the reference reflector comprises a spiral reflector, and the reference reflector and the spiral sampling reflector are rotated in synchronization with one another.

23. The method of claim 18, wherein rotating the spiral sampling reflector comprises rotating the spiral sampling reflector to reflect the sampling beam through a sheath of a catheter into the tissue.

* * * * *